United States Patent [19]

Angelier et al.

[11] Patent Number: 4,485,641

[45] Date of Patent: Dec. 4, 1984

[54] DEVICE FOR FREEZING BIOLOGICAL PRODUCTS

[75] Inventors: Nicole Angelier, Echirolles; François Colomb, Grenoble, both of France

[73] Assignee: L'Air Liquide, Societe Anonyme Pour L'Etude et L'Exploitation des Procedes Georges Claude, Paris, France

[21] Appl. No.: 510,898

[22] Filed: Jul. 5, 1983

[30] Foreign Application Priority Data

Jul. 7, 1982 [FR] France .................. 82 11896

[51] Int. Cl.³ .............................. F25B 19/00
[52] U.S. Cl. .................... 62/514 R; 62/78; 62/407; 62/414; 62/419
[58] Field of Search .............. 62/78, 514 R, 407, 414, 62/419

[56] References Cited

U.S. PATENT DOCUMENTS

| 3,442,091 | 5/1969 | Klipping et al. | 62/514 R |
| 3,902,657 | 9/1975 | Baron | 62/514 R |
| 4,304,293 | 12/1981 | Scheiwe et al. | 62/514 R |
| 4,314,450 | 2/1982 | Pelloux-Gervais | 62/78 |
| 4,386,504 | 7/1983 | Brautigam | 62/78 |

Primary Examiner—Ronald C. Capossela
Attorney, Agent, or Firm—Young & Thompson

[57] ABSTRACT

A freezing device for biological products comprises an impeller arranged at the top of a sleeve located above a basin of liquid nitrogen. The impeller causes a rising flow of nitrogen vapours within the sleeve and a descending flow outside it, the impeller and sleeve being arranged within a casing. When cooling is completed, the sleeve is lowered into the basin of liquid nitrogen. The invention is applied to the freezing of biological products stored in tubes, ampoules, phials, or straws arranged at the base of the sleeve.

4 Claims, 1 Drawing Figure

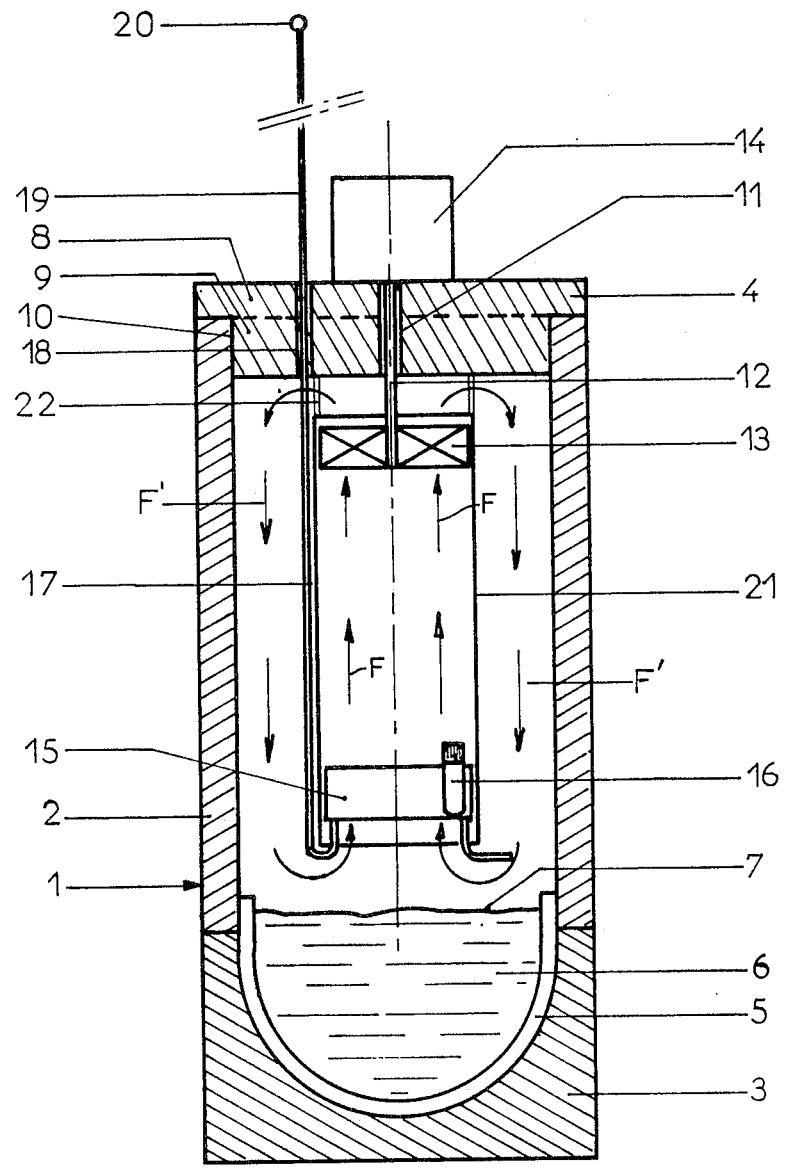

DEVICE FOR FREEZING BIOLOGICAL PRODUCTS

BACKGROUND OF THE INVENTION

The present invention relates to a device for freezing biological products stored in tubes, ampoules, phials or straws of the kind comprising a thermally insulated casing of elongated shape between a supporting base arranged to receive liquid nitrogen and a cover incorporating means of supporting the said tubes, ampoules or phials, and means for engendering a circulation of gas.

In a device of this nature, the cooling speeds are obtained in automatic manner either by controlling an electromagnetic valve placed in the liquid nitrogen supply circuit, or by controlling a heating resistance situated in the gas circuit, and the operation is conducted in accordance with a program arranged in such manner that the biological products are cooled progressively to a freezing temperature, the cooling operation continuing in gradual manner as far as the temperature required, after which said products are immersed in liquid nitrogen for preservation.

It is an object of the invention to provide a device for freezing biological products of the kind hereinabove referred to, which allows progressive cooling of biological products stored in plastic tubes, glass ampoules, phials or straws to be secured by freezing means which are uncomplicated in operation, compact, semi-automatic, inexpensive, rendering it possible to obtain predetermined and reproducible temperature decreases, to ensure an optimum rate of cell survival after freezing and storage in a bath of liquid nitrogen.

SUMMARY OF THE INVENTION

To achieve this and other objects, in accordance with the invention, the gas circulation devices comprise a gas circulation impeller driven by a variable speed motor and arranged axially in the container at a high position, and a co-axial sleeve external to the said impeller extending considerably downwards but stopping a distance from the bottom, in a unit with the said cover by means of rods, thus forming a free space between the cover and the upper part of the sleeve. In this manner, a programmed cooling operation may be provided in an uncomplicated manner for biological products in the process of being frozen, simply by varying the rotary speed of the impeller. A curve is preferably provided for converting the cooling speeds into rotary speeds of the impeller, and these obviously differ depending on whether the product is in the liquid phase or solid phase condition and they are determined for a defined quantity of products.

According to a preferred embodiment of the invention, the means for supporting the tubes, ampoules, phials or straws are provided within the said sleeve and these are preferably integral with a rod arranged to slide through the cover. Due to this system, satisfactory termination of a freezing cycle may be assured upon its completion by causing the support for the tubes, ampoules or phials to be lowered, from the outside, thereby causing these to be immersed in the liquid nitrogen bath. The reproducible nature of the freezing cycles is assured on the one hand by the fact that the liquid nitrogen level may be adjusted to a predetermined value at the beginning of a freezing cycle and that the supports for biological products are provided with a number of tubes, ampoules, phials or straws which is strictly constant as a function of the capacity of the casing and notwithstanding the quantity of biological products to be frozen.

BRIEF DESCRIPTION OF THE DRAWINGS

The features and advantages of the invention will emerge from the following description given with reference to the accompanying drawing which by way of example illustrates a view in vertical cross-section of a casing in accordance with the invention.

DETAILED DESCRIPTION OF THE PREFERRED EMBODIMENT

Referring now to the drawing, a freezing device according to the invention comprises a casing 1 having insulating walls, with a cylindrical wall 2, a bottom wall 3, and a cover 4, the bottom wall 3 incorporating a removable hemispherical basin 5 intended to receive liquid nitrogen 6 up to a level 7. The cover 4 comprises two superposed parts 8 and 9, the part 8 having a greater diameter and bearing against an upper rim 10 of the sidewall 2. The cover 4 has an axial perforation 11 to enable a driving spindle 12 of an impeller 13 placed at a high position to pass therethrough, the spindle being driven by a variable speed motor 14. Below the impeller 13 is axially positioned a carrier 15 for tubes, ampoules, phials or straws 16 which is supported by an eccentric rod 17 passing through the cover 4 at 18 in a sliding fit and having a sizeable external extension 19 terminating in a handle 20. Around the impeller 13 and the support 15 is arranged a sleeve 21 secured to the cover 4 by means of metal rods 22. This sleeve 21 is situated at a distance from the sidewall 2 in such manner as to provide a vertically rising gas flow within an internal portion of the sleeve 21 according to the arrows F and a vertically descending flow around the said sleeve along the arrows F' in the interstitial space between said sleeve and the wall 2.

It will be observed that, with the device described, the gas flow along the arrows FF' is the more voluminous, the greater the speed of revolution of the impeller 13, the latter being controllable from the outside by varying the speed of the motor 14. It will be apparent that this speed of gas flow renders it possible to obtain a cooling action on the biological products stored in the members 16, which is the faster the higher this speed.

At the end of the cooling cycle, the support 15 is lowered into a low position until it is immersed in the liquid nitrogen bath 6 by simple lowering of the actuating rod 19 handled by means of the grip 20, assuring immediate completion of the freezing operation on the biological products at −196° C.

The device which has been described is intended more particularly for laboratories which have to operate preservation equipment at low temperature for the preservation of biological products of animal or vegetable origin in the fields of medicine, pharmaceutics, biology, victualling, etc . . . .

We claim:

1. A device for freezing biological products, comprising a thermally insulated vertically elongated casing, means for supporting said biological products within the casing, a receptacle for liquid nitrogen inside the casing and at the bottom of the casing, a cover closing the top of the casing, a sleeve extending vertically within the casing but terminating downwardly a distance above the level to which liquid nitrogen may fill said receptacle, a rotary gas circulation impeller within an upper portion of the casing and having an axis of rotation which is coaxial with the sleeve, a variable speed motor for driving said impeller, and means supporting the sleeve from the cover with the upper end of the sleeve spaced below the cover to permit circulation of gaseous nitrogen in one vertical direction through the sleeve and in the opposite vertical direction outside the sleeve.

2. A device as claimed in claim 1, said supporting means supporting said biological products within said sleeve.

3. A device as claimed in claim 2, said means for supporting said biological products being in turn supported by a rod that slides vertically through said cover whereby in a raised position of the rod, said products are cooled by gaseous nitrogen and in a lowered position of said rod said products are immersed in said liquid nitrogen in said receptacle.

4. A device as claimed in claim 1, said impeller circulating gaseous nitrogen upwardly through the interior of the sleeve and downwardly about the exterior of the sleeve.

* * * * *